US008309608B2

(12) United States Patent
Zeiher et al.

(10) Patent No.: US 8,309,608 B2
(45) Date of Patent: Nov. 13, 2012

(54) USE OF ENOS TRANSCRIPTION ENHANCERS IN THE CELL THERAPY OF ISCHEMIC HEART DISEASES

(75) Inventors: Andreas Zeiher, Frankfurt am Main (DE); Stefanie Dimmeler, Frankfurt am Main (DE); Christopher Heeschen, Frankfurt am Main (DE); Hartmut Ruetten, Idstein (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 2160 days.

(21) Appl. No.: 10/979,399

(22) Filed: Nov. 2, 2004

(65) Prior Publication Data

US 2005/0101599 A1 May 12, 2005

Related U.S. Application Data

(60) Provisional application No. 60/583,622, filed on Jun. 29, 2004.

(30) Foreign Application Priority Data

Nov. 6, 2003 (EP) .................................... 03025512

(51) Int. Cl.
*A61K 31/165* (2006.01)

(52) U.S. Cl. .................. 514/617; 514/235.5; 514/237.8; 514/249; 514/255.06; 514/256; 514/274; 514/311; 514/331; 514/337; 514/341; 514/343; 514/344; 514/349; 514/350; 514/352; 514/354; 514/355; 514/365; 514/374; 514/378; 514/383; 514/399; 514/406; 514/418; 514/423; 514/428; 514/464; 514/465; 514/466; 514/618; 514/619; 514/622; 424/93.7

(58) Field of Classification Search ........................ 548/1
See application file for complete search history.

(56) References Cited

U.S. PATENT DOCUMENTS

| 6,617,359 | B2 | 9/2003 | Strobel |
| 6,759,412 | B2 | 7/2004 | Strobel |
| 6,812,253 | B2 | 11/2004 | Strobel |
| 6,949,556 | B2 | 9/2005 | Strobel |
| 7,105,513 | B2 | 9/2006 | Strobel |
| 7,179,839 | B2 | 2/2007 | Strobel |
| 7,186,735 | B2 | 3/2007 | Strobel |
| 7,202,278 | B2 | 4/2007 | Strobel |
| 2004/0082628 | A1 | 4/2004 | Strobel |
| 2004/0092513 | A1 | 5/2004 | Strobel |
| 2004/0110808 | A1 | 6/2004 | Strobel |
| 2007/0082897 | A1 | 4/2007 | Strobel |

OTHER PUBLICATIONS

Reffelmann et. al., Cellular cardiomyoplasty—cardiomyocytes, skeletal myoblasts, or stem cells for regenerating myocardium and treatment of heart failure?, Cardiovascular Research, 2003, 58:358-368.*
Aicher, et al., Essential role of endothelial nitric oxide synthase for mobilization of stem and progenitor cells, Nat. Med. 2003; 9: 1370-1376.
Assmus, et al., Transplantation of progenitor cells and regeneration enhancement in acute myocardial infarction (TOPCARE-AMI), , Circulation 2002, 106:3009-3017.
Britten, et al., Infarct remodeling after intracoronary progenitor cell treatment in patients with acute myocardial infarction (TOPCARE-AMI), , Circulation 2003, 108:2212-2218.
Edelberg, et al., Young adult bone marrow-derived endothelial precursor cells restore aging-impaired cardiac angiogenic function, Circ. Res. 2002, 90:e89-e93.
Fuchs, et al., Catheter-based autologous bone marrow myocardial injection in no-option patients with advanced coronary artery disease: a feasibility study, J. Am. Coll. Cardiol. 2003, 41:1721-1724.
Heeschen, Christopher et al., Profoundly Reduced Neovascularization Capacity of Bone Marrow Mononuclear Cells Derived From Patients With Chronic Ischemic Heart Disease, Circulation, (2004), vol. 109, pp. 1615-1622.
Huige, Li et al., Activation of Protein Kinase C Alpha and/or Epsilon Enhances Transcription of the Human Endothelial Nitric Oxide Synthase Gene , Molecular Pharmacology, (1998), vol. 53, pp. 630-637.
Iwaguro, Hideki et al., Endothelial Progenitor Cell Vascular Endothelial Growth Factor Gene Transfer for Vascular Regeneration, Circulation, (2002), vol. 105, pp. 732-738.
Kalka, Christoph et al., Transplantation of ex vivo expanded endothelial progenitor cells for therapeutic neovascularization, PNAS, (2000), vol. 97, No. 7, pp. 3422-3427.
Kocher, A. A. et al., Neovascularization of ischemic myocardium by human bone-marrow-derived angioblasts prevents cardiomyocyte apoptosis, reduces remodeling and improves cardiac function, Nature Medicine, (2001), vol. 7, No. 4, pp. 430-436.
Lee, Sang H. et al., Early Expression of Angiogenesis Factors in Acute Myocardial Ischemia and Infarction, New England Journal Med., (2000), vol. 342, pp. 626-633.
Murasawa, Satoshi et al., Constitutive Human Telomerase Reverse Transcriptase Expression Enhances Regenerative Properties of Endothelial Progenitor Cells, Circulation, (2002), vol. 106, pp. 1133-1139.
Orlic, Donald et al., Bone marrow cells regenerate infarcted myocardium, Nature, (2001), vol. 410, pp. 701-705. Strauer, Bodo E. et al., Repair of Infarcted Myocardium by Autologous Intracoronary Mononuclear Bone Marrow Cell Transplantation in Humans, Circulation, (2002), vol. 106, pp. 1913-1918.
Sasaki, et al., Ex Vivo Pretreatment of Bone Marrow Mononuclear Cells with Endothelial NO Synthase Enhancer AVE9488 Enhances their Functional Activity for Cell Therapy, PNAS (2006) vol. 33 No. 39 pp. 14537-14541.
Knowles, et al., Enhanced Atherosclerosis and Kidney Dysfunction in eNOS-/-Apoe-/-mice are ameliorated by Enalapril Treatment, J. Clin. Invest.; (105), 2000, pp. 451-458.
Kuhlencordt, et al., Accelerated Atherosclerosis, Aortic Aneurysm Formation, and Ischemic Heart Disease in Apolipoprotein E/Endothelial Nitric Oxide Synthase Double-Knockout Mice, Circulation; (104); 2001; pp. 448-454.
Ozaki, et al., Overexpression of Endothelial Nitric Oxide Synthase Accelerates Atherosclerotic Lesion Formation in apoE-deficient Mice, J. Clin. Invest.; (110); 2002; pp. 331-340.

* cited by examiner

*Primary Examiner* — Daniel Sullivan
*Assistant Examiner* — Barbara Frazier
(74) *Attorney, Agent, or Firm* — Scully, Scott, Murphy & Presser, P.C.

(57) ABSTRACT

The present invention relates to the use of compounds which enhance the transcription of endothelial nitric oxide synthase (eNOS) for treating stem and progenitor cells in the cell therapy of patients with ischemic heart diseases such as coronary heart disease or ischemic cardiomyopathy. Treatment of such cells which are isolated from bone marrow, for example, with an eNOS transcription enhancer prior to their administration improves their functional activity and ameliorates neovascularization of the heart and cardiac regeneration.

8 Claims, No Drawings

USE OF ENOS TRANSCRIPTION ENHANCERS IN THE CELL THERAPY OF ISCHEMIC HEART DISEASES

This application claims the benefit of U.S. Provisional Application No. 60/583,622, filed Jun. 29, 2004, which is incorporated by reference herein.

The present invention relates to the use of compounds which enhance the transcription of endothelial nitric oxide synthase (eNOS) for treating stem and progenitor cells in the cell therapy of patients with ischemic heart diseases such as coronary heart disease or ischemic cardiomyopathy. Treatment of such cells which, for example, can be isolated from bone marrow, with an eNOS transcription enhancer prior to their administration improves their functional activity and ameliorates neovascularization of the heart and cardiac regeneration.

Post infarction heart failure remains a major cause of morbidity and mortality in patients with an ischemic heart disease such as coronary heart disease or ischemic cardiomyopathy. Although prompt reperfusion of the occluded artery has significantly reduced early mortality rates, ventricular remodeling processes characterized by progressive expansion of the infarct area and dilation of the left ventricular cavity often result in the development of heart failure in patients surviving an acute myocardial infarction. The major goal to reverse remodeling would be the stimulation of neovascularization as well as the enhancement of regeneration of cardiac myocytes within the infarct area.

Recent research results have established a fundamental role for endothelial stem and progenitor cells in postnatal neovascularization and cardiac regeneration. Improvement of neovascularization after critical ischemia is an important therapeutic option after events such as myocardial infarction or limb ischemia, for example. Until recently, neovascularization of ischemic tissue in the adult was believed to be restricted to migration and proliferation of mature endothelial cells, a process termed angiogenesis. Meanwhile, increasing evidence suggests that circulating endothelial progenitor cells (EPCs) home to sites of ischemia and contribute to the formation of new blood vessels (C. Kalka et al., Transplantation of ex vivo expanded endothelial progenitor cells for therapeutic neovascularization, Proc. Natl. Acad. Sci. USA 2000, 97:3422-7). In analogy to the embryonic development of blood vessels from primitive endothelial progenitors (angioblasts), this process is referred to as vasculogenesis. The importance of circulating progenitor cells is demonstrated by the fact that genetic inhibition of their recruitment inhibits tumor angiogenesis. EPCs can be mobilized from the bone marrow into the circulation by vascular endothelial growth factor (VEGF) or stromal cell-derived factor (SDF)-1. Both VEGF and SDF-1 are profoundly upregulated in hypoxic tissue suggesting that VEGF and SDF-1 constitute homing signals to recruit circulating progenitor cells to enhance endogenous repair mechanisms after critical ischemia (S. H. Lee et al., Early expression of angiogenesis factors in acute myocardial ischemia and infarction, N. Engl. J. Med. 2000, 342:626-33).

Recent experimental studies support that progenitor cells obtained from bone marrow or blood contribute to the regeneration of infarcted myocardium and enhance neovascularization of ischemic myocardium (A. A. Kocher et al., Neovascularization of ischemic myocardium by human bone-marrow-derived angioblasts prevents cardiomyocyte apoptosis, reduces remodeling and improves cardiac function, Nat. Med. 2001, 7:430-6; D. Orlic et al., Bone marrow cells regenerate infarcted myocardium, Nature 2001, 410: 701-5; S. Fuchs et al., Catheter-based autologous bone marrow myocardial injection in no-option patients with advanced coronary artery disease: a feasibility study, J. Am. Coll. Cardiol. 2003, 41:1721-4). Moreover, intravenous infusion or intramyocardial injection of adult progenitor cells resulted in sustained improvement of cardiac function both after experimentally induced myocardial infarction and in patients with chronic ischemic heart disease. It has been clinically demonstrated that intracoronary infusion of adult stem and progenitor cells is feasible and safe both in patients with acute myocardial infarction and in patients with chronic ischemic cardiomyopathy (B. Assmus et al., Transplantation of progenitor cells and regeneration enhancement in acute myocardial infarction (TOPCARE-AMI), Circulation 2002, 106:3009-17; B. E. Strauer et al., Repair of infarcted myocardium by autologous intracoronary mononuclear bone marrow cell transplantation in humans, Circulation 2002, 106: 1913-8). Such a cell therapy, which in a patient is performed as an autologous cell therapy, is associated with significant improvements in regional and global left ventricular function.

A prerequisite for the success of cell therapy of patients with an ischemic heart disease is the homing and, thus, engraftment of the transplanted cells into the target area in the heart, especially if an intravascular route of administration is chosen. Whereas the number of bone marrow stem and progenitor cells of various types such as mesenchymal and hematopoietic stem and progenitor cells is similar in patients with an ischemic heart disease and healthy controls, unfortunately the functional activity of the stem and progenitor cells from patients with an ischemic heart disease is impaired and their homing capacity decreased. This functional impairment of stem and progenitor cells from patients with coronary heart disease limits their therapeutic potential for clinical cell therapy. This applies especially when an intravascular route of administration is used which requires the progenitor cells to extravasate against a chemoattractant gradient in order to invade and home to ischemic tissue. The functional activity and homing capacity of stem and progenitor cells can be assessed by determining their colony forming activity or migratory activity, for example in response to VEGF or SDF-1. Monitoring the migratory or colony forming activity of stem and progenitor cells prior to cell therapy can serve as a surrogate test for identifying patients who may derive greater benefit from cell therapy. On the other hand, it has recently been described that fully functional bone marrow-derived EPCs from healthy donor mice restore the senescent host cardiac angiogenesis in a murine model of impaired neovascularization (J. M. Edelberg et al., Young adult bone marrow-derived endothelial precursor cells restore aging-impaired cardiac angiogenic function, Circ. Res. 2002, 90:e89-e93). Thus, it would be advantageous if by suitable means, for example by pharmacological or genetic manipulation prior to administration, the activity of the functionally impaired stem and progenitor cells from patients with ischemic heart diseases could be restored and thereby the patients' therapeutic benefit from cell therapy be enhanced.

Surprisingly, it has been found that the impaired function of stem and progenitor cells from patients with an ischemic heart disease can be improved considerably by incubation with a transcription enhancer of endothelial nitric oxide synthase. Enhanced expression of endothelial nitric oxide synthase, produced by ex vivo treatment of the patients' cells with an eNOS transcription enhancer prior to their readministration, improves or restores the functional activity of these cells as has been demonstrated both in vitro using a transmigration assay and in vivo in a murine model of hind limb ischemia as outlined below. In the latter model the neovascularization after ligation of the femoral artery is determined via blood flow measurement, and it has been found that the beneficial effect of administered stem and progenitor cells from patients with ischemic heart disease if substantially increased after pretreatment with an eNOS transcription enhancer. That the observed effect is indeed caused by the enhanced activity of endothelial NO synthase and NO formation has been proven by the abrogating effect of $N^G$-monomethyl-L-arginine (L-NMMA) which is known to be an inhibitor of eNOS and NO formation. Incubation of the stem and progenitor cells from patients with an ischemic heart disease in the presence of both an eNOS transcription enhancer and L-NMMA did not bring about an improved functional activity.

Thus, a subject of the present invention is the use of a transcription enhancer of endothelial nitric oxide synthase for treating stem and/or progenitor cells in the cell therapy of a patient with an ischemic heart disease, as well as the use of a transcription enhancer of endothelial nitric oxide synthase for the production of a medicament for treating stem and/or progenitor cells in the cell therapy of a patient with an ischemic heart disease, and a process for producing a medicament for treating stem and/or progenitor cells in the cell therapy of a patient with an ischemic heart disease, comprising employing a transcription enhancer of endothelial nitric oxide synthase, and a method of treating stem and/or progenitor cells in the cell therapy of a patient with an ischemic heart disease which comprises the treatment of the cells with a transcription enhancer of endothelial nitric oxide synthase.

Endothelial NO synthase (eNOS, NOS-III) belongs to a group of three isoenzymes which produce the messenger molecule nitric oxide (nitrogen monoxide; NO) by oxidation of arginine. Endothelium-derived NO is of central importance in a number of key cardiovascular mechanisms. It has a vasodilating effect and inhibits the aggregation of platelets, the adhesion of leukocytes to the endothelium and the proliferation of intimal smooth muscle cells. Endothelial NO synthase is subject to physiological and pathophysiological regulation both at the transcriptional and at the post-transcriptional level. Upregulation of eNOS expression in endothelial cells is an effective means of treating and preventing various conditions including cardiovascular diseases such as coronary heart disease and atherogenesis. Compounds which enhance eNOS transcription are described in WO 02/064146, WO 02/064545, WO 02/064546 and WO 02/064565, for example. The beneficial effect on the functional capacity of stem and progenitor cells brought about by the ex vivo treatment of such cells in the cell therapy of patients with ischemic heart diseases is not described in these references. The importance of eNOS for the mobilization of stem and progenitor cells from bone marrow into the circulatory system has recently been described (A. Aicher et al., Essential role of endothelial nitric oxide synthase for mobilization of stem and progenitor cells, Nat. Med. 2003; 9: 1370-1376).

In a preferred embodiment of the present invention the eNOS transcription enhancers are used which are disclosed in WO 02/064146, WO 02/064545, WO 02/064546 and WO 02/064565 and corresponding patent documents such as U.S. 2003/0008915, U.S. 2003/0022935, U.S. 2003/0022939 and U.S. 2003/0055093 the contents of which are incorporated herein by reference. In a more preferred embodiment of the present invention an eNOS transcription enhancer of the formula I is used,

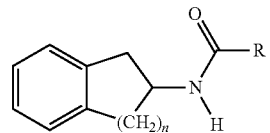

in which n is 1, 2 or 3;

R is phenyl or the group Hetar both of which are unsubstituted or carry one, two, three or four identical or different substituents selected from the group consisting of F; Cl; Br; $C_1$-$C_3$-alkyl; $C_1$-$C_3$-alkoxymethyl; 2-amino-3,3,3-trifluoropropyl-; $CF_3$; $C_3$-$C_5$-alkandiyl; phenyl; heteroaryl; benzyl; heteroaryl-methyl-; OH; $C_1$-$C_3$-alkoxy; phenoxy; trifluoromethoxy; 2,2,2-trifluoroethoxy; ($C_1$-$C_4$-alkyl)COO; ($C_1$-$C_3$-alkyl)mercapto; phenylmercapto; ($C_1$-$C_3$-alkyl)sulfonyl; phenylsulfonyl; $NH_2$; ($C_1$-$C_4$-alkyl)amino; di($C_1$-$C_4$-alkyl)amino; ($C_1$-$C_3$-alkyl)-CONH—; ($C_1$-$C_3$-alkyl)-$SO_2$NH—; ($C_1$-$C_3$-alkyl)-CO; phenyl-CO; —OCH$_2$O—; —OCF$_2$O—; —CH$_2$CH$_2$O—; COO($C_1$-$C_4$-alkyl); —CONH$_2$; —CONH($C_1$-$C_4$-alkyl); —CON(di($C_1$-$C_4$-alkyl)); CN; —SO$_2$NH$_2$; —SO$_2$NH($C_1$-$C_4$-alkyl); —SO$_2$N(di($C_1$-$C_4$-alkyl)); pyrrolidinyl; piperidinyl; morpholinyl; and thiomorpholinyl; wherein all heteroaryl, phenyl, heteroaryl-containing and phenyl-containing groups, which are optionally present in the said substituents of the said phenyl or the said group Hetar, are unsubstituted or substituted by one, two, three or four identical or different substituents selected from the group consisting of F, Cl, Br, CN, $C_1$-$C_3$-alkyl, OH, $C_1$-$C_3$-alkoxy, and $CF_3$;

heteroaryl and the group Hetar independently of one another are a 5-membered to 10-membered, aromatic, monocyclic or bicyclic heterocycle containing one, two, three or four identical or different heteroatoms selected from the group consisting of N, O and S;

in any of its stereoisomeric forms or a mixture thereof in any ratio, or a pharmaceutically acceptable salt thereof.

If in the compounds of formula I groups or substituents such as, for example, phenyl, heteroaryl, alkyl etc., can be present several times, they all independently from each other have the meanings indicated and can hence, in each case, be identical to or different from each other. An example is the di($C_1$-$C_4$-alkyl)amino group in which the alkyl substituents can be identical or different.

Alkyl residues can be linear or branched, acyclic or cyclic. This also applies when they are part of other groups, for example alkoxy groups, alkoxycarbonyl groups or amino groups, or when they are substituted.

Examples of alkyl groups are methyl, ethyl, propyl, butyl, the n-isomers of these residues, isopropyl, isobutyl, sec-butyl, tert-butyl. The term alkyl here also expressly includes cycloalkyl residues and cycloalkyl-alkyl-residues (alkyl substituted by cycloalkyl) containing at least three carbon atoms. Examples for such cycloalkyl residues are cyclopropyl and cyclobutyl. Cycloalkyl groups can be substituted by one or more identical or different ($C_1$-$C_4$)-alkyl residues, in particular by methyl. Furthermore, unless stated otherwise, the term alkyl here also includes unsubstituted alkyl residues as well as alkyl residues which are substituted by one or more, for example one, two, three or four, identical or different residues, for example phenyl groups. In substituted alkyl residues, for example phenylalkyl, the substituents can be present in any desired position.

Examples of $C_3$-$C_5$-alkandiyl are —CH$_2$CH$_2$CH$_2$—, —CH$_2$—CH(CH$_3$)—, —CH$_2$CH$_2$CH$_2$CH$_2$— and —CH$_2$CH$_2$CH$_2$CH$_2$CH$_2$— groups.

If not stated otherwise, the above-mentioned phenyl residues and heterocyclic residues including heteroaryl residues can be unsubstituted or can carry one, two, three or four of the substituents indicated in the above definition which can be present in any desired position. In monosubstituted phenyl residues the substituent can be in the 2-position, the 3-position or the 4-position, in disubstituted phenyl residues the substituents can be in 2,3-position, 2,4-position, 2,5-position, 2,6-position, 3,4-position or 3,5-position. In trisubstituted phenyl residues the substituents can be in 2,3,4-position, 2,3,5-position, 2,3,6-position, 2,4,5-position, 2,4,6-position or 3,4,5-position. In fourfold substituted phenyl residues, the substituents can be in the 2,3,4,5-position, the 2,3,4,6-position, or the 2,3,5,6-position.

Unless stated otherwise, heteroaryl residues and heterocyclic residues such as the group Hetar are preferably derived from heterocycles which contain one, two or three identical or different heteroatoms, more preferably from heterocycles which contain one or two identical or different heteroatoms. The rings in heterocyclic groups preferably are 5-membered rings, 6-membered rings or 7-membered rings, more preferably 5-membered rings or 6-membered rings. Examples of monocyclic and bicyclic heterocyclic systems from which residues occurring in the compounds of the formula I can be derived, are pyrrole, furan, thiophene, imidazole, pyrazole, 1,2,3-triazole, 1,2,4-triazole, 1,3-dioxole, 1,3-oxazole (=oxazole), 1,2-oxazole (=isoxazole), 1,3-thiazole (=thiazole), 1,2-thiazole (=isothiazole), tetrazole, pyridine, pyridazine, pyrimidine, pyrazine, pyran, thiopyran, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine, 1,3-thiazepine, indole, benzothiophene, benzofuran, benzothiazole, benzoimidazole, benzodioxole, quinoline, isoquinoline, cinnoline, quinazoline, quinoxaline, phthalazine, thienothiophenes, 1,8-naphthyridine and other naphthyridines, pteridin, or phenothiazine, each of them in saturated form (perhydro form), or in partially unsaturated form (for example in the dihydro form or the tetrahydro form) or in maximally unsaturated form, in case the respective forms are known and stable and comprised by the definition of the compounds. The term heteroaryl as used herein comprises bicyclic residues in which both cycles are aromatic as well as bicyclic residues in which only one cycle is aromatic. Independently, the same applies to the group Hetar. Suitable heterocycles include, for example, the saturated heterocycles pyrrolidine, piperidine, morpholine and thiomorpholine. Unsaturated heterocycles can contain, for example, one, two or three double bonds within the ring system. 5-membered rings and 6-membered rings can in particular also be aromatic.

Substituents which may be derived from these heterocycles can be attached via any suitable carbon atom. Residues derived from nitrogen heterocycles which carry a hydrogen atom or a substituent on a ring nitrogen atom, for example pyrrole, imidazole, pyrrolidine, morpholine, piperazine, can also be attached via a ring nitrogen atom, in particular if the respective heterocyclic residue is bonded to a carbon atom. For example, a thienyl residue can be present as 2-thienyl residue or 3-thienyl residue, a furyl residue as 2-furyl residue or 3-furyl residue, a pyridyl residue as 2-pyridyl residue, 3-pyridyl residue or 4-pyridyl residue, a piperidinyl residue as 1-piperidinyl residue (=piperidino residue), 2-piperidinyl residue, 3-piperidinyl residue or 4-piperidinyl residue, a (thio)morpholinyl residue as 2-(thio)morpholinyl residue, 3-(thio)morpholinyl residue or 4-(thio)morpholinyl residue (=thiomorpholino residue). A residue derived from 1,3-thiazole or imidazole which is attached via a carbon atom can be attached via the 2-position, the 4-position or the 5-position.

In case a heterocyclic group is substituted, it can carry one, two, three or four identical or different substituents. Substituents in heterocycles can be present in any desired positions, for example in a 2-thienyl residue or 2-furyl residue in the 3-position and/or in the 4-position and/or in the 5-position, in a 3-thienyl residue or 3-furyl residue in the 2-position and/or in the 4-position and/or in the 5-position, in a 2-pyridyl residue in the 3-position and/or in the 4-position and/or in the 5-position and/or in the 6-position, in a 3-pyridyl residue in the 2-position and/or in the 4-position and/or in the 5-position and/or in the 6-position, in a 4-pyridyl residue in the 2-position and/or in the 3-position and/or in the 5-position and/or in the 6-position. Suitable nitrogen heterocycles can also be present as N-oxides or as quarternary salts containing a counterion which is derived from a pharmaceutically acceptable acid. Pyridyl residues, for example, can be present as pyridine-N-oxides.

The present invention includes all stereoisomeric forms of the compounds of the formula I. Centers of asymmetry that are present in the compounds of formula I all independently of one another can have S configuration or R configuration. The invention includes all possible enantiomers and diastereomers and mixtures of two or more stereoisomers, for example mixtures of enantiomers and/or diastereomers, in all ratios. Thus, compounds used according to the present invention which can exist as enantiomers can be present in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. All these forms are comprised by the present invention. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of the formula I or at the stage of an intermediate during the synthesis. The present invention also includes all tautomeric forms of the compounds of formula I.

In case the compounds according to formula I contain one or more acidic or basic groups, the invention also comprises their corresponding pharmaceutically or toxicologically acceptable salts, in particular their pharmaceutically utilizable salts. Thus, the compounds of the formula I which contain acidic groups can be present on these groups and can be used according to the invention, for example, as alkali metal salts, alkaline earth metal salts or as ammonium salts. More specific examples of such salts include sodium salts, potassium salts, calcium salts, magnesium salts or salts with ammonia or organic amines such as, for example, ethylamine, ethanolamine, triethanolamine or amino acids. Compounds of the formula I which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula I simultaneously contain acidic and basic groups in the molecule, the invention also includes, in addition to the salt forms mentioned, inner salts or betaines (zwitterions). The respective salts can be obtained from the compounds of the formula I by customary methods which are known to the person skilled in the art like, for example, by contacting them with an organic or inorganic acid or base in a solvent or dispersant, or by anion exchange or cation exchange with other salts.

The present invention furthermore includes the use of solvates of compounds of the formula I, for example hydrates or adducts with alcohols, and active metabolites of the compounds of the formula I, and of derivatives and prodrugs of the compounds of the formula I which contain physiologically tolerable and cleavable groups, for example esters, amides and compounds in which the N—H group depicted in formula I is replaced with an N-alkyl group, such as N-methyl, or with an N-acyl group, such as N-acetyl or N-argininyl, including pharmaceutically acceptable salts formed on functional groups present in the N-acyl group, provided they exhibit the desired activity when used according to the present invention under conditions suitable for ex vivo treatment of stem and progenitor cells.

Particularly preferably compounds of the formula I are used according to the present invention in which one or more of the variables therein have the preferred meanings given below, with all combinations of preferred meanings being a subject of the present invention. With respect to all preferred compounds of the formula I the present invention also includes the use of all stereoisomeric forms and mixtures thereof in all ratios, and of their pharmaceutically acceptable salts.

n, i. e. the number of $CH_2$ groups in the polymethylene chain $(CH_2)_n$, preferably is 1 or 3. In one embodiment of the invention a compound of the formula I is used in which n is 1, i. e. the indan-2-yl amide of an acid of the formula R—COOH. In another embodiment of the invention a compound of the formula I is used in which n is 3, i. e. the 6,7,8,9-tetrahydro-5H-benzocyclohepten-6-yl amide of an acid of the formula R—COOH.

R is preferably selected from 4-fluorophenyl, 4-chlorophenyl, 4-bromophenyl, 4-($C_1$-$C_3$-alkoxy)phenyl, 4-trifluoromethoxyphenyl, 2-bromo-4-fluorophenyl, 2-chloro-4-fluorophenyl, 3,4-dimethylphenyl, 2,4-dimethylphenyl, 4-chloro-2-methylphenyl, 2-hydroxy-4-methylphenyl, 2-hydroxy-4-ethoxyphenyl, 2-methoxy-4-methylphenyl, 4-phenoxyphenyl, 3-fluoro-4-methylphenyl, benzo[1,3]dioxol-5-yl, 2,2-difluorobenzo[1,3]dioxol-5-yl, 2,3-dihydrobenzofuran-5-yl, 1-(4-chlorophenyl)-5-trifluoromethyl-1H-pyrazole-4-yl, 1-(4-fluorophenyl)-3,5-dimethyl-1H-pyrazole-4-yl, 1H-benzotriazole-5-yl, 1H-indole-4-yl, 1H-indole-6-yl, 1-isopropyl-2-trifluoromethyl-1H-benzoimidazole-5-yl, 1-methyl-3-oxo-1,2,3,4-tetrahydro-quinoxaline-6-yl, 1-phenyl-5-trifluoromethyl-1H-pyrazole-4-yl, 2-(2-hydroxypyridin-4-yl)-1H-benzoimidazole-5-yl, 2-(4-cyanophenyl)-1H-benzoimidazole-5-yl, 2,4-dimethyloxazole-5-yl, 2,4-dimethylpyrimidine-5-yl, 2,4-dimethylthiazole-5-yl, 2,5-dimethyl-1H-pyrrole-3-yl, 2,5-dimethyl-1-phenyl-1H-pyrrole-3-yl, 2,5-dimethyl-1-pyridin-4-ylmethyl-1H-pyrrolyl, 2,5-dimethyl-2H-pyrazole-3-yl, 2,6-dichloropyrid-3-yl, 2,6-dimethoxypyrid-3-yl, 2,6-dimethylpyrid-3-yl, 2-amino-4,6-dimethylpyrid-3-yl, 2-amino-6-chloropyrid-3-yl, 2-amino-pyrid-3-yl, 2-chloro-6-methylpyrid-3-yl, 2-chloropyrid-4-yl, 2-cyclopropyl-4-methyl-thiazole-5-yl, 2-dimethylamino-4-methyl-thiazole-5-yl, 2-dimethylaminopyrid-4-yl, 2-ethyl-5-methyl-2H-pyrazole-3-yl, 2-hydroxy-6-methylpyrid-3-yl, 2-methyl-1H-benzoimidazole-5-yl, 2-methyl-3H-benzoimidazole-5-yl, 2-methylpyrid-3-yl, 2-methyl-6-trifluoromethylpyrid-3-yl, 2-methylthiazole-5-yl, 2-(morpholin-4-yl)pyridin-4-yl, 2-(morpholin-4-yl)pyrimidine-5-yl, 2-(pyrrolidin-1-yl)pyridin-4-yl, 3,5-dimethyl-1H-pyrazole-4-yl, 3-amino-5,6-dimethylpyrazine-2-yl, 3-amino-5-methylpyrazine-2-yl, 3-aminopyrazine-2-yl, 3-dimethylamino-4-methylphenyl, 3-dimethylaminophenyl, 3H-benzoimidazole-5-yl, 1H-benzoimidazole-5-yl, 3-methanesulfonylamino-2-methylphenyl, 3-methanesulfonylaminophenyl, 3-methyl-isoxazole-4-yl, 3-(morpholin-4-yl)phenyl, 3-(piperidin-1-yl)phenyl, 3-(pyrrolidin-1-yl)phenyl, 4-(2,2,2-trifluoroethoxy)phenyl, 4,6-dimethylpyrid-3-yl, 4-amino-2-ethylsulfanylpyrimidine-5-yl, 4-amino-2-methylpyrimidine-5-yl, 4-chloro-3-methanesulfonylamino-phenyl, 4-chloro-3-sulfamoylphenyl, 4-methyl-3-methylaminophenyl, 4-methylthiazole-5-yl, pyrid-2-yl, 5,6,7,8-tetrahydroquinoline-3-yl, 5-amino-1-phenyl-1H-pyrazole-4-yl, 5-methanesulfonyl-2-methylphenyl, 5-methyl-1-phenyl-1H-pyrazole-4-yl, 5-methylisoxazole-3-yl, 5-methylpyrid-3-yl, 5-methylpyrazine-2-yl, 6-chloropyrid-3-yl, 6-cyanopyrid-3-yl, 6-dimethylaminopyrid-3-yl, 6-ethynylpyrid-3-yl, 6-methoxymethylpyrid-3-yl, 6-methoxypyrid-3-yl, 6-methyl-2-methylaminopyrid-3-yl, 6-methylaminopyrazine-2-yl, 6-methylpyrid-3-yl, 6-(morpholin-4-yl)pyrid-3-yl, 6-(pyrrolidin-1-yl)pyrid-3-yl, imidazo[1,2-a]pyridine-2-yl, 6-trifluoromethylpyrid-3-yl, and pyrimidine-4-yl.

Heteroaryl is preferably a 5-membered to 10-membered, aromatic, monocyclic or bicyclic heterocycle containing one, two or three, more preferably one or two, identical or different heteroatoms selected from the group consisting of N, O and S. Heteroaryl is most preferably selected from the group consisting of furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzodioxolyl, benzoimidazolyl, benzothiazolyl, benzoxazolyl, quinolinyl, isoquinolinyl, quinoxalinyl, quinazolyl, indolyl, benzofuranyl, benzothiophenyl, and indazolyl.

The group Hetar is preferably 5-membered to 10-membered, aromatic, monocyclic or bicyclic heterocycle containing one, two or three, more preferably one or two, identical or different heteroatoms selected from the group consisting of N, O and S. The group Hetar is most preferably selected from the group consisting of furyl, pyrrolyl, thienyl, thiazolyl, isothiazolyl, oxazolyl, isoxazolyl, pyrazolyl, imidazolyl, pyridazinyl, pyrazinyl, pyridyl, pyrimidinyl, benzodioxolyl, benzoimidazolyl, benzothiazolyl, benzoxazolyl, quinolinyl, isoquinolinyl, quinoxalinyl, quinazolyl, indolyl, benzofuranyl, benzothiophenyl, and indazolyl.

In an especially preferred embodiment of the present invention a compound of the formula I is used in which the number n is 1 and the group R has one of the above-listed meanings from which R is preferably selected, in any of its stereoisomeric forms or a mixture thereof in any ratio, or a pharmaceutically acceptable salt thereof. In another especially preferred embodiment of the present invention a compound of the formula I is used in which the number n is 3 and the group R has one of the above-listed meanings from which R is preferably selected, in any of its stereoisomeric forms or a mixture thereof in any ratio, or a pharmaceutically acceptable salt thereof. Examples of such especially preferred compounds of the formula I are 4-fluoro-N-(indan-2-yl)benzamide and 2,2-difluorobenzo[1,3]dioxol-5-carboxylic acid indan-2-ylamide.

The compounds used according to the present invention, specifically the compounds of the formula I, and their precursors can be synthesized according to methods described in the literature or analogous methods known to one skilled in the art. Compounds of the formula I can be synthesized, for example, from the respective acid of the formula R—COOH or a derivative thereof and the respective amine by forming an amide bond. To this end, the respective amine can be dissolved in an inert solvent like, for example, water, isopropanol, dichloromethane, tetrahydrofuran, toluene or dioxane and reacted in the presence of base like, for example, triethylamine or sodium hydroxide, with an appropriate carboxylic acid derivative, for example a carboxylic acid chloride, for example at room temperature. The compounds according to the formula I can also be obtained by a coupling reaction of the respective amine with the respective acid in the presence of a base like, for example, diisopropylethylamine, and an appropriate coupling reagent like, for example, a carbodiimide, such as dicyclohexylcarbodiimide, or TOTU, in an inert solvent like, for example, tetrahydrofuran, dioxane or dimethylformamide, for example at room temperature. If desired, the obtained acylamine can then be functionalized to obtain further compounds. All reactions for the synthesis of the compounds of the formula I are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York. Depending on the circumstances of the individual case, in order to avoid side reactions during the synthesis of a compound of the formula I, it can be necessary or advantageous to temporarily block functional groups by introducing protective groups and to deprotect them in a later stage of the synthesis, or introduce functional groups in the form of precursor groups, for example a nitro group which is a precursor of an amino group, which in a later reaction step are converted into the desired functional groups. Such synthesis strategies and protective groups and precursor groups which are suitable in an individual case are known to the skilled person. If desired, the compounds of the formula I can be purified by customary purification procedures, for example by recrystallization or chromatography. The starting compounds for the preparation of the compounds of the formula I are commercially available or can be prepared according to or analogously to literature procedures.

The isolation and further handling of the adult stem and progenitor cells which are treated with an eNOS transcription enhancer according to the present invention can be carried out according to standard methods which are described in the literature, or analogously to methods described in the literature, and are well known to one skilled in the art. The employed cells can be obtained from bone marrow of the patient which is gained by the usual aspiration procedure, and can thus be bone marrow stem and progenitor cells or bone marrow-derived stem and progenitor cells. The bone marrow is worked up by the usual procedure which can include a fractionation by density gradient centrifugation to isolate mononuclear cells. After washing, the cells are suspended in a usual cell culture medium, for example a commercially available X-Vivo medium (Cambrex, East Rutherford, N.J., USA) which is a serum free-medium and is suitable for application in humans. As another cell culture medium in which the cells can be suspended for the further handling, which is suitable for experimental investigation, the commercially available RPMI 1640 medium (Sigma, St. Louis, Mo., USA) may be mentioned. Generally, the obtained cell suspension consists of heterogenous cell populations including hematopoietic progenitor cells. The obtained cell suspension can be characterized and, for example, hematopoietic and mesenchymal stem and progenitor cell populations identified by standard techniques such as flow cytometry analysis using customary antibodies. The functional activity of the cells can be assessed, for example, in a colony forming units assay or by determining their migratory capacity in response to VEGF or SDF-1 as mentioned above and outlined in more detail below. The cell suspension contains cells which are or which can develop into endothelial progenitor cells which in turn can develop into endothelial cells and elicit the formation of new blood vessels, i. e. promote neovascularization of the infarct area. Besides from bone marrow, progenitor cells used according to the present invention can also be obtained, for example, from fat tissue or from circulating blood of the patient by similar procedures to give adipose tissue-derived progenitor cells or circulating blood-derived progenitor cells, respectively. Cell populations obtained from the blood are usually cultured ex vivo for several days before readministration. As endothelial progenitor cells present in the systemic circulation are derived from bone marrow cells, a term like "bone-marrow derived" can properly be used to refer to cells obtained from bone marrow of the patient as well as to cells obtained from collected blood.

The ex vivo treatment of the obtained suspension of stem and progenitor cells from patients with ischemic heart diseases for improving their impaired functional activity and homing capacity and thus the neovascularization after their readministration, can be performed under standard conditions for cell culturing. The concentration of the cells in the suspension, which may be a suspension in a suitable medium such as X-Vivo, for example, which is a complete formulation and does not require the addition of further substances, may be in the range from about 100000 per ml to about 5000000 per ml, for example about 1000000 per ml. The pH of the medium used for the treatment with the eNOS expression enhancer generally is in the range from about 6.5 to about 7.5, in particular from about 6.8 to about 7.3, as is the pH throughout the handling of the cells. The cell suspension is admixed with a solution of the eNOS transcription enhancer in a suitable, pharmaceutically acceptable solvent, for example water or an organic solvent such as an alcohol like ethanol or a polyglycol like polypropylene glycol or dimethylsulfoxide or a mixture of such solvents. The solution of the eNOS transcription enhancer may also contain pharmaceutically acceptable auxiliaries such as salts, buffer substances or solubilizers. The concentration of the eNOS transcription enhancer in the resulting mixture generally is from about 1 nM to about 1 mM, in particular from about 0.1 µM to about 100 µM, for example from about 1 µM to about 10 µM such as about 5 µM. The mixture is then incubated under sterile conditions at a temperature which usually is about 37° C., in a humid atmosphere which may consist of air containing about 5% of carbon dioxide, for example. The incubation period depends on the circumstances of the individual case, for example the efficacy of the employed eNOS transcription enhancer. Generally it is from about 6 hours to about 48 hours, for example from about 12 hours to about 24 hours such as about 18 hours. If progenitor cells obtained from circulating blood are used according to the invention, the incubation with the eNOS transcription enhancer can take place during the above-mentioned cultivation that is usually performed with such cells. The obtained mixture can directly be administered to the patient without workup as the contained eNOS transcription enhancer is a drug substance which also exerts favorable effects in the body. Alternatively, the treated cells can first be separated from the obtained mixture by centrifugation, washed, for example with buffer solution, resuspended again, for example in a medium such as X-Vivo, and this suspension administered to the patient.

A further subject of the present invention is the before-described process for producing stem and/or progenitor cells with improved functional activity by treatment with an eNOS transcription enhancer, i. e. a process for producing stem and/or progenitor cells with improved functional activity, comprising treating stem and/or progenitor cells from a patient with an ischemic heart disease with a transcription enhancer of endothelial nitric oxide synthase. Subjects of the present invention also are a medicament (or pharmaceutical composition or pharmaceutical preparation) which comprises an eNOS transcription enhancer, for example a compound of the formula I and/or a pharmaceutically acceptable salt thereof, and optionally one or more auxiliaries such as salts or buffer substances or solubilizers, for use in the treatment of stem and progenitor cells in the cell therapy of a patient with an ischemic heart disease, as well as a kit or package for use in such treatment which contains such a medicament together with further items for such use, for example a suitable solvent or medium for dissolving a solid eNOS transcription enhancer, and instructions for use. The medicament may, for example, comprise a solid eNOS transcription enhancer contained in a bottle, an ampoule or a vial which is then dissolved prior to the addition of the eNOS transcription enhancer to the cell suspension, or a solution of an eNOS transcription enhancer which can directly be added to the cell suspension.

The suspension of the stem and/or progenitor cells obtained after treatment with the eNOS transcription enhancer can be administered to the patient systemically by intravenous injection or infusion or directly into the heart or into blood vessels close to the heart by intramyocardial injection or intracoronary injection or infusion, for example. Administration directly into the infarcted myocard or into coronary blood vessels can take place during surgery or via a catheterization procedure as outlined below in more detail. The suitable administration procedures are established in the art and well known to the skilled person.

The term ischemic heart disease as used herein is to be understood as comprising any heart disease in which an insufficient blood supply to one or more regions of the myocard occurs or has occurred or in which an amelioration of neovascularization or neoangiogenesis is desired by the physician, and includes diseases such as, for example, coronary heart disease, coronary artery disease, acute coronary syndrome, angina pectoris, myocardial infarction, ischemic cardiomyopathy and congestive heart failure which latter disease can be due to an ischemia. An ischemic heart disease that can be treated according to the present invention can be an acute or chronic disease.

EXAMPLES

Synthesis of eNOS Transcription Enhancers 4-fluoro-N-(indan-2-yl)benzamide 43.70 g (258 mmol) of 2-aminoindane hydrochloride and 53.43 g (528 mmol) of triethylamine were added to 250 ml of tetrahydrofuran, 42.89 g (270 mmol) of 4-fluorobenzoyl chloride were added, and the mixture was stirred for 2 hours at room temperature. The resulting mixture was then poured onto an ice/HCl mixture, the obtained precipitate was filtered, washed with a $NaHCO_3$ solution and water and dried in vacuo. The crude product was crystallized from methanol. Yield: 47.8 g (73%) of a white crystalline product.

Melting point: 167° C.

Mass spectrum: 256.1 [M+H$^+$]

$^1$H-NMR spectrum (300 MHz, $d_6$-DMSO): 2.96 (dd, 2H, H1/3), 3.25 (dd, 2H, H3/1), 4.70 (sextett, 1H, H2), 7.12-7.19 (m, 2H, H4,7/5,6), 7.20-7.28 (m, 2H, H5,6/4,7), 7.30 (t, 2H, H3', 5'), 7.95 (dd, 2H, H2',6'), 8.68 (d, 1H, NH).

Further compounds of the formula I were synthesized according to procedures such as the following exemplary general procedures A, B and C.

Procedure A 0.5 mmol (96 mg) of 1-ethyl-3-(3-(dimethylamino)propyl) carbodiimide hydrochloride and 0.5 mmol (87 µl) of diisopropylethylamine (DIPEA) were dissolved in 2.5 ml of dichloromethane (DCM), added to a solution of 0.5 mmol of the respective acid in 2.5 ml of DCM and stirred for 10 minutes at room temperature. Then 0.7 mmol of the respective amine were added and stirring was continued over night. The resulting solution was then washed 2 times with 2N HCl and once with a saturated $KHCO_3$-solution, dried over $MgSO_4$ and filtered. The residue obtained after evaporating to dryness was crystallized from an ethyl acetate/hexane or a methanol/diethyl ether mixture or purified by HPLC.

Procedure B

To 0.75 mmol of the respective acid and 271 µl (1.575 mmol) of DIPEA in 5 ml of tetrahydrofuran were given 271 mg (0.825 mmol) of O-[(cyano-ethoxycarbonyl-methylene) amino]-N,N,N',N'-tetramethyluronium tetrafluoroborate (TOTU) (dissolved in 1 ml of dimethylformamide (DMF)). After 15 minutes stirring at room temperature a mixture of 0.9 mmol of the respective amine hydrochloride and 172 µl (1 mmol) of DIPEA in 1 ml of DMF was added. After stirring for 6 hours the mixture was filtered and evaporated. The residue was taken up in ethyl acetate and washed successively with 20 ml of 1N of HCl and 20 ml of 5% sodium hydrogencarbonate solution. The resulting organic phase was evaporated and purified by preparative HPLC (RP 18, acetonitrile/water).

Procedure C 2.5 mmol of the respective amine were mixed with 550 mg of triethylamine and 5 ml of dioxane, then 2.5 mmol of the respective carboxylic acid chloride was added and the mixture stirred at room temperature over a period of 2 hours. The resulting mixture was then poured onto an ice/HCl mixture, the obtained precipitate was extracted with ethyl acetate, dried with sodium sulfate and concentrated. The thus-obtained residue was fractionated by preparative HPLC.

As an example of the prepared compounds the following one is mentioned.

2,2-difluorobenzo[1,3]dioxol-5-carboxylic acid indan-2-ylamide

Melting point: 147.5° C.

Mass spectrum: 318.2 [M+H$^+$]

$^1$H-NMR spectrum (400 MHz, d6-DMSO): 2.91-2.99 (m, 2H, H-1/H-3), 3.22-3.30 (m, 2H, H-3/H-1), 4.69 (sext., 1H, H-2), 7.13-7.19 (m, 2H, H-4, H-7 or H-5, H-6), 7.21-7.28 (m, 2H, H-4, H-7 or H-5, H-6), 7.50 (d, 1H, H-6'/H7'), 7.80 (d, 1H, H-7'/H6), 7.88 (s, 1H, H4'), 8.71 (d, 1H, NH).

Measurement of Activation of eNOS Transcription

Activation of eNOS transcription was measured as described in detail in Li et al., Activation of protein kinase C alpha and/or epsilon enhances transcription of the human endothelial nitric oxide synthase gene, Mol. Pharmacol. 1998, 53:630-637. Briefly, a 3.5 kB long fragment 5' of the starting codon of the eNOS gene was cloned, sequenced and cloned in firefly luciferase expression plasmids to monitor activation of the eNOS promoter by reporter gene activity. A human endothelial cell line stable transfected and expressing this promoter-reporter construct was used for compound testing. Cells were incubated for 18 hours with compounds. All compounds were dissolved before in sterile dimethylsulfoxide (DMSO). A final concentration of 0.5% DMSO in complete medium was allowed. Induction of reporter gene expression in these cells was measured using a standard luciferase assay system (Promega, Madison, Wis., USA; Cat. No E150) according to the manufacturer's instructions. Luciferase induction in cells incubated with compounds were compared to those incubated with solvent alone. The ratio of both activities (transcription induction ratio, TIR) was plotted as a function of compound concentration. Typically, TIR values started at low concentrations at a ratio of 1, indicating no compound effect, and extended up to a maximum TIR value TIR(max) which indicates the increase of the eNOS transcription. $EC_{50}$ values of transcription induction ratios as a function of compound concentration were determined graphically.

Isolation of Bone Marrow Cells

Bone marrow aspirates were collected from a total of 9 healthy controls and 25 patients with stable coronary heart disease and a history of myocardial infarction at the age between 18 and 75 years. Patients had to have regional wall motion abnormalities, a patent native vessel, coronary artery bypass graft, or collateral artery. Since myocardial ischemia is known to mobilize bone marrow-derived progenitor cells, patients with evidence for inducible or resting myocardial ischemia during the past 4 weeks were excluded. Further exclusion criteria were the presence of active or chronic infection, operations or trauma within the last two months, evidence for malignant diseases, active gastrointestinal bleeding, uncontrollable hypertension over 160/100 mm Hg, stroke within the last two years, AV-aneurysm, renal or hepatic insufficiency, thrombocytopenia with platelet counts<100000/µl, anemia with hemoglobin<8.5 g/dl, mental retardation, enrollment in another clinical trial, or unwillingness to participate. Also excluded were pregnant and premenopausal women. The ethics review board of the Hospital of the Johann Wolfgang Goethe University of Frankfurt, Germany, approved the protocol, and the study was conducted in accordance with the Declaration of Helsinki. Written informed consent was obtained from each patient.

A total of 50 ml bone marrow aspirate was obtained from each participant. Bone marrow stem and progenitor cells were isolated by density gradient centrifugation. After two washing steps, cells were resuspended in 10 ml X-vivo 10 medium (without gentamicin and phenol red; Cambrex, East Rutherford, N.J., USA). The cell suspension consists of heterogeneous cell populations including hematopoietic progenitor cells.

The bone marrow stem and progenitor cells were analyzed by means of flow cytometry. For the identification of hematopoietic and mesenchymal stem and progenitor cell populations, directly conjugated antibodies against human CD45 (Becton Dickinson, Franklin Lakes, N.J., USA), CD34 (FITC-labeled; BD Pharmingen, San Diego, Calif., USA), CD133 (APC-labeled; BD Pharmingen), CD14 (FITC-labeled; BD Pharmingen), CXCR4 (APC-labeled, BD Pharmingen), and CD49d (APC-labeled; BD Pharmingen) were used. The lineage panel was obtained from BD Pharmingen (containing FITC-labeled CD3, CD14, CD16, CD19, CD20, and CD56) and was completed by additionally using directly FITC-conjugated antibodies against CD15 and glycophorin A (both from BD Pharmingen).

Treatment of Bone Marrow Cells with eNOS Transcription Enhancers

For incubation with the eNOS transcription enhancer 4-fluoro-N-(indan-2-yl)benzamide, 1 ml of a suspension of 1000000 stem and progenitor cells in 1 ml of X-Vivo 10 cell culture medium was mixed with 1 µl of a solution of 4-fluoro-N-(indan-2-yl)benzamide in dimethylsulfoxide (DMSO) which had been prepared by dissolution of 1.275 mg of 4-fluoro-N-(indan-2-yl)benzamide in 1 ml of DMSO. The concentration of 4-fluoro-N-(indan-2-yl)benzamide in the resulting mixture was 5 µM. For incubation with the eNOS transcription enhancer 4-fluoro-N-(indan-2-yl)benzamide and the eNOS inhibitor $N^G$-monomethyl-L-arginine (L-NMMA), in addition to 4-fluoro-N-(indan-2-yl)benzamide, L-NMMA (Sigma, St. Louis, Mo., USA) was added to the cell suspension to give a resulting mixture with a 4-fluoro-N-(indan-2-yl)benzamide concentration of 5 µM and an L-NMMA concentration of 1 mM. Incubation was carried for 18 hours at a temperature of 37° C. under an atmosphere of air containing 5% of carbon dioxide. The cells were isolated by centrifugation, washed two times with PBS and resuspended in X-Vivo 10.

Measurement of the Functional Activity of Bone Marrow Cells

For assessing the colony forming activity, bone marrow stem and progenitor cells ($1 \times 10^5$ per dish) were seeded in methylcellulose plates (Methocult GF H4535 including stem cell factor, granulocyte colony-stimulating factor, granulocyte macrophage colony-stimulating factor, interleukin-3, interleukin-6; CellSystems, St. Katharinen, Germany). Plates were studied under phase contrast microscopy, and colony forming units granulocyte-macrophage (CFU-GM; colonies>50 cells) were counted after 14 days of incubation.

For assessing the migratory capacity of bone marrow stem and progenitor cells, a total of $1 \times 10^6$ bone marrow stem and progenitor cells were resuspended in 250 µl of X-Vivo 10 and placed in the upper chamber of a modified Boyden chamber filled with matrigel (BioCoat invasion assay, 8 µm pore size, Becton Dickinson Labware, Two Oak Park, Bedford, Mass., USA). Then, the chamber was placed in a 24-well culture plate containing 500 µl endothelial basic medium (EBM) supplemented with either phosphate buffered saline (PBS), 50 ng/ml VEGF, or 100 ng/ml SDF-1. After 24 hours incubation at 37° C., transmigrated cells were counted.

In vivo Hind Limb Ischemia Model in Mice

The neovascularization capacity of bone marrow stem and progenitor cells was investigated in a murine model of hind limb ischemia by use of 8 to 10 week old athymic NMRI nude mice (The Jackson Laboratory, Bar Harbor, Me., USA) weighing 18 to 22 g. The proximal portion of the femoral artery including the superficial and the deep branch as well as the distal portion of the saphenous artery were ligated with 7-0 silk suture. All arterial branches between the ligation were obliterated using an electrical coagulator. The overlying skin was closed using three surgical staples. After 24 hours, a suspension of bone marrow stem and progenitor cells in X-Vivo 10 was intravenously injected ($5 \times 10^4$, $5 \times 10^5$, or $5 \times 10^6$ cells/mouse; n=5 per group). After two weeks the limb perfusion was determined. Specifically, the ischemic (right) limb/normal (left) limb blood flow ratio was measured using a laser Doppler blood flow meter (Laser Doppler Perfusion Imager System, MoorLDI-Mark 2, Moor Instruments, Wilmington, Del., USA). Before initiating scanning, mice were placed on a heating plate at 37° C. to minimize variations in temperature. After twice recording laser Doppler color images, the average perfusions of the ischemic and non-ischemic limb were calculated on the basis of colored histogram pixels. To minimize variables including ambient light and temperature, calculated perfusion was expressed as the ratio of ischemic to non-ischemic hind limb perfusion.

For histological evaluation, the tissue vascularization was determined in 5 μm frozen sections of the adductor and semimembranous muscles from the ischemic and the non-ischemic limb. Endothelial cells were stained with FITC-labeled monoclonal antibody directed against CD146 (Chemicon, Temecula, Calif., USA). Capillary density is expressed as number of capillaries/myocyte. Human bone marrow stem and progenitor cells were identified by co-staining with HLA-DR-APC-labeled antibodies (BD Pharmingen, San Diego, Calif., USA) and CD146-FITC-labeled antibodies.

Administration of Bone Marrow Cells to Patients

The administration of bone marrow cells treated with an eNOS transcription enhancer to a patient can be performed by the following catheterization procedure for progenitor cell transplantation. An over-the-wire balloon catheter oversized by 0.5 mm is advanced into a stent previously implanted. To allow for adhesion and potential transmigration of the infused cells through the endothelium, the balloon is inflated with low pressure to completely block blood flow for 3 minutes, while 3.3 ml of the progenitor cell suspension is infused distally to the occluding balloon through the central port of the balloon catheter. This procedure is repeated 3 times to accommodate infusion of a total of 10 ml of progenitor cell suspension, interrupted by 3 minutes of reflow by deflating the balloon to minimize extensive ischemia. After completion of intracoronary cell transplantation, coronary angiography is repeated to ascertain vessel patency and unimpeded flow of contrast material.

The statistical analysis was performed by standard methods. If not stated otherwise, results for continuous variables are expressed as means±standard deviation. Comparisons between groups were analyzed by t test (two-sided) or ANOVA for experiments with more than two subgroups. Post hoc range tests and pair wise multiple comparisons were performed with the t test (two-sided) with Bonferroni adjustment. Comparison of categorical variables was generated by the Pearson $x^2$ test. After blind assessment of the in vitro characteristics of the bone marrow stem and progenitor cells, test results were merged with the results from the in vivo studies. To identify in vitro determinants of bone marrow stem and progenitor cells for their in vivo neovascularization capacity, a multivariate linear regression analysis for was performed. P values<0.05 were considered statistically significant. All analyses were performed with SPSS 11.5 (SPSS Inc., Chicago, Ill., USA).

The following results were obtained.

Measurement of Activation of eNOS Transcription

The compound 4-fluoro-N-(indan-2-yl)benzamide exhibited in the luciferase assay for activation of eNOS transcription an $EC_{50}$ value of 0.8 μM and a TIR(max) value of 4.10.

The compound 2,2-difluorobenzo[1,3]dioxol-5-carboxylic acid indan-2-ylamide exhibited in the luciferase assay for activation of eNOS transcription an $EC_{50}$ value of 0.14 μM and a TIR(max) value of 2.7.

Measurement of the Functional Activity of Bone Marrow Cells

The colony forming activity of bone marrow stem and progenitor cells from the patients was 37.3±25.0 CFU-GM/dish versus 113.8±70.4 CFU-GM/dish for the cells from the healthy controls (P=0.009).

The migratory response to VEGF of bone marrow stem and progenitor cells from the patients was 34.0±24.2×1000 migrated cells versus 54.8±29.3×1000 migrated cells for the cells from the healthy controls (P=0.027).

The migratory response to SDF-1 of bone marrow stem and progenitor cells from the patients was 46.3±26.2×1000 migrated cells versus 108.6±40.4×1000 migrated cells for the cells from the healthy controls (P<0.001).

The migratory response to SDF-1 of bone marrow stem and progenitor cells from the healthy controls after 18 hours of treatment with PBS was 126.5.3±41.7×1000 migrated cells versus 111.2±38.5×1000 migrated cells for the cells from the healthy controls after 18 hours of treatment with 4-fluoro-N-(indan-2-yl)benzamide (5 μM) (P<0.01).

The migratory response to SDF-1 of bone marrow stem and progenitor cells from the patients after 18 hours of treatment with PBS was 38.0±13.7×1000 migrated cells versus 74.0±20.7×1000 migrated cells for the cells from the patients after 18 hours of treatment with 4-fluoro-N-(indan-2-yl)benzamide (5 μM) (P<0.01).

The migratory response to SDF-1 of bone marrow stem and progenitor cells from the patients after 18 hours of treatment with 4-fluoro-N-(indan-2-yl)benzamide (5 μM) and $N^G$-Monomethyl-L-arginine (L-NMMA) (1 mM) was 23.9±7.4×1000 migrated cells versus 74.3±21.5×1000 migrated cells for the cells from the healthy controls after 18 hours of treatment with 4-fluoro-(N-indan-2-yl)benzamide (5μM) (P<0.01).

In vivo Hind Limb Ischemia Model in Mice

The comparison of the effect of the stem and progenitor cells was performed at a cell concentration of $5 \times 10^5$ cells/mouse at which concentration the maximal therapeutic effect with bone marrow stem and progenitor cells from healthy controls was achieved.

In the various test groups the following laser Doppler-derived relative blood flow values (blood flow ratio ischemic (right) limb/normal (left) limb in percent) was determined after administration of bone marrow stem and progenitor cells as specified.

| | | |
|---|---|---|
| No cells | 21.9 ± 10.8% | n = 11 |
| Cells from healthy controls | 72.7 ± 18.7% | n = 24 |
| Cells from the patients, untreated | 40.7 ± 12.2% | n = 24 |
| Cells from the patients, treated for 18 hours with 5 μM 4-fluoro-N-(indan-2-yl)benzamide | 59.1 ± 11.6%* | n = 24 |
| Cells from the patients, treated for 18 hours with 5 μM 4-fluoro-N-(indan-2-yl)benzamide and 1 mM L-NMMA | 39.7 ± 10.3% | n = 18 |

*P < 0.001 versus cells from the patients, untreated

We claim:

1. A method for treating stem or progenitor cells of a patient suffering from an ischemic heart disease in a cell therapy comprising ex vivo treating stem or progenitor cells of the patient with a transcription enhancer of endothelial nitric oxide synthase.

2. The method according to claim 1, wherein the transcription enhancer of endothelial nitric oxide synthase is a compound of formula I

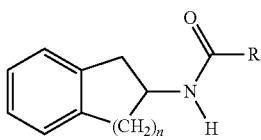

wherein:

n is 1, 2 or 3;

R is phenyl or the group Hetar, each of which is unsubstituted or substituted by one, two, three or four identical or different substituents selected from the group consisting of F; Cl; Br; $C_1$-$C_3$-alkyl; $C_1$-$C_3$-alkoxymethyl; 2-amino-3,3,3-trifluoropropyl-; $CF_3$; $C_3$-$C_5$-alkandiyl; phenyl; heteroaryl; benzyl; heteroaryl-methyl-; OH; $C_1$-$C_3$-alkoxy; phenoxy; trifluoromethoxy; 2,2,2-trifluoroethoxy; ($C_1$-$C_4$-alkyl)COO—; ($C_1$-$C_3$-alkyl)mercapto; phenylmercapto; ($C_1$-$C_3$-alkyl)sulfonyl; phenylsulfonyl; $NH_2$; ($C_1$-$C_4$-alkyl)amino; di($C_1$-$C_4$-alkyl) amino; ($C_1$-$C_3$-alkyl)-CONH—; ($C_1$-$C_3$-alkyl)-$SO_2$NH—; ($C_1$-$C_3$-alkyl)-CO—; phenyl-CO—; —$OCH_2O$—; —$OCF_2O$—; —$CH_2CH_2O$—; COO($C_1$-$C_4$-alkyl); —$CONH_2$; —CONH($C_1$-$C_4$-alkyl); —CON(di($C_1$-$C_4$-alkyl)); CN; —$SO_2NH_2$; —$SO_2$NH($C_1$-$C_4$-alkyl); —$SO_2$N(di($C_1$-$C_4$-alkyl)); pyrrolidinyl; piperidinyl; morpholinyl; and thiomorpholinyl; wherein the heteroaryl and phenyl moieties in the substituents independently are unsubstituted or substituted by one, two, three or four identical or different substituents selected from the group consisting of F, Cl, Br, CN, $C_1$-$C_3$-alkyl, OH, $C_1$-$C_3$-alkoxy, and $CF_3$; and heteroaryl and the group Hetar independently of one another are a 5-membered to 10-membered, aromatic, monocyclic or bicyclic heterocycle containing one, two, three or four identical or different heteroatoms selected from the group consisting of N, O and S;

or its stereoisomeric form or a mixture of stereoisomeric forms in any ratio, or a pharmaceutically acceptable salt thereof.

3. The method according to claim 1, wherein the transcription enhancer of endothelial nitric oxide synthase is selected from 4-fluoro-N-(indan-2-yl)benzamide and 2,2-difluorobenzo[1,3]dioxol-5-carboxylic acid indan-2-ylamide.

4. The method according to claim 1, wherein the stem or progenitor cells are obtained from bone marrow of the patient.

5. The method according to claim 1, wherein the stem or progenitor cells are incubated with the transcription enhancer of endothelial nitric oxide synthase for a period of from 6 hours to 48 hours.

6. The method according to claim 1, wherein the ischemic heart disease is coronary heart disease, coronary artery disease, acute coronary syndrome, angina pectoris, myocardial infarction, ischemic cardiomyopathy, or congestive heart failure.

7. A method for treating a patient suffering from an ischemic heart disease comprising administering to the patient in a cell therapy stem or progenitor cells of the patient wherein the cells were ex vivo treated with a transcription enhancer of endothelial nitric oxide synthase.

8. The method according to claim 7, wherein the administering to the patient the treated stem or progenitor cells is by intravenous, intracoronary or intramyocardial injection or infusion.

* * * * *